United States Patent [19]

Siegemund et al.

[11] 4,287,124
[45] Sep. 1, 1981

[54] PROCESS FOR THE PREPARATION OF 4,5-PERFLUORO-1,3-DIOXALANES

[75] Inventors: Günter Siegemund, Hofheim am Taunus; Herbert Muffler, Frankfurt am Main, both of Fed. Rep. of Germany

[73] Assignee: Hoechst Aktiengesellschaft, Frankfurt am Main, Fed. Rep. of Germany

[21] Appl. No.: 122,691

[22] Filed: Feb. 19, 1980

[30] Foreign Application Priority Data

Feb. 20, 1979 [DE] Fed. Rep. of Germany ....... 2906447

[51] Int. Cl.$^3$ ............................................ C07D 317/10
[52] U.S. Cl. ............................................ 260/340.9 R
[58] Field of Search ................................. 260/340.9 R

[56] References Cited

U.S. PATENT DOCUMENTS

| | | | |
|---|---|---|---|
| 2,260,261 | 10/1941 | Morey | 260/340.9 R |
| 3,475,456 | 10/1969 | Selman | 260/340.9 R |
| 3,475,457 | 10/1969 | Sianesi et al. | 260/340.9 R |
| 3,629,323 | 12/1971 | Selman et al. | 260/340.9 R X |
| 3,758,510 | 9/1973 | Delavarenne | 260/340.9 R |

*Primary Examiner*—Ethel G. Love
*Attorney, Agent, or Firm*—Curtis, Morris & Safford

[57] ABSTRACT 4,5-Perfluoro-1,3-dioxolanes prepared by the described process have an anesthetic effect.

5 Claims, No Drawings

PROCESS FOR THE PREPARATION OF 4,5-PERFLUORO-1,3-DIOXALANES

It is known that the reaction of perfluoroalkene epoxides with ketones yields 2,2-dialkyl-4,5-perfluoro-1,3-dioxolanes. The examples disclosed by H. S. Eleuterio in J.Macromol.Sci.Chem. A6(6), 1027 (1972) and DE-OS No. 1,543,786 reveal, however, that the process can be carried out only with ketones as carbonyl compounds. Highly reactive epoxides such as

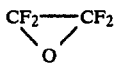

are required as starting components, which could be produced so far exclusively in admixture with the basic perfluoroolefin, i.e. $CF_2=CF_2$, and which cannot be handled in pure state on an industrial scale. If less reactive perfluoroalkene epoxides such as

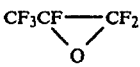

are used the known process requires a reaction time of several days to obtain yields of 2,2-dialkyl-4,5-perfluoro-1,3-dioxolanes in the range of from 16 to 39% of the theory.

The present invention provides a process for the manufacture of 4,5-perfluoro-1,3-dioxolanes of the formula I

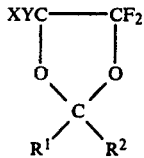

in which X and Y, independent of one another, denote fluorine or trifluoromethyl and $R^1$ and $R^2$ are hydrogen or methyl, by reacting a 2-(α-chloroalkoxy)-perfluorocarboxylic acid halide of the formula II $$R^1R^2CCl-O-CXY-COZ \quad II$$

in which X, Y, $R^1$ and $R^2$ are as defined under formula I and Z denotes chlorine or fluorine, with a fluoride of an element of main groups I or II of the Periodic Table, with ammonium or with an alkylammonium fluoride.

The reaction takes place according to the scheme

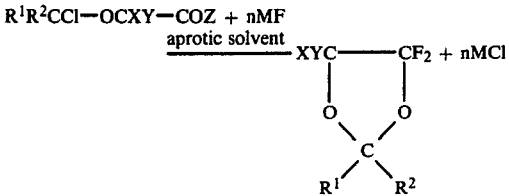

in which n is 1 if Z denotes fluorine and n is 2 if Z denotes chlorine and MF denotes the fluorides defined above.

The starting components of the formula II used in the process of the invention can be prepared by chlorination under the action of light of 2-alkoxy-perfluorocarboxylic acid halides described in the literature (cf. DE-OS No. 1,793,240) or by usual methods from known 2-alkoxy-perfluorocarboxylic acid esters, such as conversion into the corresponding sodium salt, alkaline saponification of the esters (cf. D. Sianesi et al., J.Org.Chem. 31, pages 2312-2316 (1966)), with subsequent reaction with an inorganic acid chloride such as $POCl_3$ or $SOCl_2$.

Suitable fluorides in the process of the invention are alkali metal fluorides such as KF and CsF, which are used in the presence or absence of HF or crown ethers, ammonium fluoride or alkyl-substituted ammonium fluorides such as $R'NH_2.HF$, $R_2'NH.HF$, $R_3'N.HF$ or $R_4'NF$ in which $R'$ denotes methyl, ethyl, n- or i-propyl or n-butyl. KF and trialkyl-substituted ammonium fluorides such as $(CH_3)_3N.HF$, $(C_2H_5)_3N.HF$ and $(n-C_4H_9)_3N.HF$ are preferred.

The process of the invention can be carried out without solvent or in an aprotic-polar solvent at temperatures of from $-20°$ C. to $+160°$ C., preferably $0°$ C. to $120°$ C. and more preferably $20°$ C. to $100°$ C. The reaction takes place without application of excess pressure and, after a relatively short reaction time, good to very good yields of 4,5-perfluoro-1,3-dioxolanes of the formula I are obtained.

The fluorides specified above are used in equivalent amounts or in an excess, preferably an excess of 10 to 50 mol % for each gram-atom of chlorine present per mol of 2-(α-chloroalkoxy)-perfluorocarboxylic acid halide.

Aprotic-polar solvents to be used, if any, are nitriles such as acetonitrile, n-butyronitrile or benzonitrile; acid amides such as formamide, dimethyl formamide, hexamethylphosphoric acid trisamide or N-methylpyrrolidone; polyethers such as 1,4-dioxane, dimethoxyethane or diethylene glycol dimethyl ether (Diglyme); dimethyl sulfoxide or sulfolane.

For the exothermal reaction it is immaterial whether the salt-like fluoride is first introduced into the reaction vessel, and then dissolved or suspended in the aprotic solvent and the 2-(α-chloroalkoxy)-perfluorocarboxylic acid halide is added to the solution or suspension or in a reverse order of succession the salt-like fluoride is added to the 2-(α-chloroalkoxy)-perfluorocarboxylic acid halide or the solution thereof in an aprotic solvent. In either case the reaction heat should be dissipated by thorough stirring and external cooling.

According to a preferred mode of operation the fluoride is first dissolved in an aprotic-polar solvent, the 2-(α-chloroalkoxy)-perfluorocarboxylic acid halide is then added dropwise while stirring and cooling with ice, the reaction mixture is heated to reflux temperature and the 4,5-perfluoro-1,3-dioxolane formed is distilled off.

It has been surprising that the reaction of 2-(α-chloroalkoxy)-perfluorocarboxylic acid halides of the formula II with alkali metal or ammonium fluorides does not yield, as could be expected, 2-(α-fluoroalkoxy)-perfluorocarboxylic acid fluorides ($R^1R^2CF-O-CXY-COF$ with $R^1$ and $R^2$ being H, $CH_3$ and XY being F, $CF_3$) under the reaction conditions according to the invention and with chlorine-fluorine exchange, but leads to the formation of 4,5-perfluoro-1,3-dioxolanes of the formula I.

It is another object of the present invention to provide 4,5-perfluoro-1,3-dioxolanes of the formula I

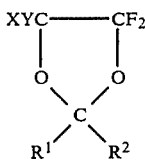

in which, independent of one another, X and Y denote fluorine or trifluoromethyl and $R^1$ is hydrogen and $R^2$ is hydrogen or methyl. More particularly, the invention provides 4,4,5,5-tetrafluoro-1,3-dioxolane, 4,4,5,5-tetrafluoro-2-methyl-1,3-dioxolane, 4,5,5-trifluoro-4-trifluoromethyl-1,3-dioxolane and 4,5,5-trifluoro-2-methyl-4-trifluoromethyl-1,3-dioxolane.

The 4,5-perfluoro-1,3-dioxolanes of the formula I obtained by the process of the invention are colorless liquids with ethereal odor which are stable to acid as well as basic hydrolysis. They are readily soluble in organic solvents and miscible to a small extent only with water.

In mammals the 4,5-perfluoro-1,3-dioxolanes of the formula I have an anesthetic or sedative effect when they are inhaled or injected and, therefore, they can be used as anesthetics. They can be used either alone or in admixture with other inhalation anesthetics such as nitrous oxide or diethyl ether, or with other anesthetic and therapeutic agents such as muscle relaxants, barbiturates and plasma expanders as often required in modern combination narcosis.

The following examples illustrate the invention.

EXAMPLE 1

A 2 liter, four-necked flask with thermometer, KPG stirrer, dropping funnel and 90 cm Vigreux column with 90 cm fractionating column is charged with 980 g (8.1 mols) of $(C_2H_5)_3N.HF$ in 1,250 ml of dry acetonitrile. 876 g of $ClCH_2$—O—$CF_2$—COF are then added dropwise over a period of 75 minutes whereby the temperatures rises to 42° C. and $(C_2H_5)_3N.HCl$ separates as precipitate. While heating the reaction mixture for 5 hours to 86° C., 610 g of distillate with a boiling range of 38° to 80° C. is obtained. A subsequent fractional distillation over a packed column yields 429 g (2.94 mols) of 4,4,5,5-tetrafluoro-1,3-dioxolane boiling at 41° to 43° C. under 750 torr.

Yield 54.5% of theory.

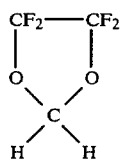

Molecular weight: 146.
Calc.: C 24.65%; H 1.37%; F 52.0%; Found: C 24.7%; H 1.5%; F 51.8%.

Under the same reaction conditions 4,4,5,5-tetrafluoro-2-methyl-1,3-dioxolane boiling at 55° C. under 750 torr can also be obtained.

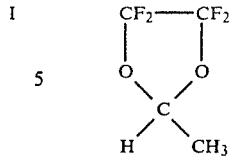

Molecular weight: 160.
Calc.: C 30.0%; H 2.5%; F 47.5%; Found: C 30.2%; H 2.4%; F 45.5%.
Yield 85% of the theory.

EXAMPLE 2

A 500 ml four-necked flask provided with KPG stirrer, thermometer, dropping funnel and Vigreux column with distillation head is charged with 58 g (1 mol) of dry and pulverized KF in 150 ml of acetonitrile and 108 g (0.66 mol) of $ClCH_2$—O—$CF_2$—COF are added dropwise. Next, the reaction mixture is heated to 80° C. and the 4,4,5,5-tetrafluoro-1,3-dioxolane formed is distilled off. After a reaction period of 13 hours and after a water treatment 94% (0.62 gramion) of the chloride to be expected can be detected. The yield of redistilled 4,4,5,5-tetrafluoro-1,3-dioxolane, boiling at 41° to 43° C. under 745 torr amounts to 74 g (76% of the theory).

EXAMPLE 3

In a 2 liter flask with KPG stirrer, thermometer, dropping funnel and Vigreux column with fractionating column 608 g (5 mols) of $(C_2H_5)_3N.HF$ are dissolved in 700 ml of dry acetonitrile and 507 g (2.21 mols) of $ClCH_2$—O—$CF(CF_3)COCl$ are added dropwise while stirring and cooling in an ice bath. The mixture is then heated for 8 hours to 82° C. whereby the reaction product distills off. The 4,5,5-trifluoro-4-trifluoromethyl-1,3-dioxolane is rectified once more. It then boils at 60° C. under 753 torr. The amount of 333 g (1.7 mols) obtained corresponds to a yield of 77% of the theory.

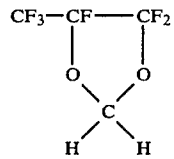

Molecular weight: 196.
Calc.: C 24.5%; H 1.02%; F 58.1%; Found: C 24.6%; H 1.10%; F 56.4%.

EXAMPLE 4

A 1 liter flask provided with KPG stirrer, thermometer, dropping funnel and Vigreux column with fractionating column is charged with a solution of 308 g (1.5 mols) of $(n-C_4H_9)_3N.HF$ in 200 ml of dry dimethyl formamide. 135 g (0.59 mol) of $CF_3CF(OCH_2Cl)COCl$ are added while stirring over a period of 1.5 hours, whereupon the internal temperature rises to 45° C. A precipitate of $(n-C_4H_9)_3N.HCl$ does not form. Upon slow heating to 130° C. 4,5,5-trifluoro-4-trifluoromethyl-1,3-dioxolane distills off. Under reduced pressure (down to 10 mm Hg) further product can be obtained. After distillation of the crude product (72 g) 62 g or 54% of pure 4,5,5-trifluoro-4-trifluoromethyl-1,3-dioxolane boiling at 60° to 61° C. under 744 torr are obtained.

EXAMPLE 5

In a 1 liter four-necked flask provided with thermometer, dropping funnel and Vigreux column with fractionating column and discharge head 182 g (1.5 mols) of $(C_2H_5)_3N.HF$ are dissolved in 400 ml of dry dioxane. 162 g (0.71 mol) of $CF_3CF(OCH_2Cl)COCl$ are then added dropwise at a temperature of from 27° to 40° C., whereupon $(C_2H_5)_3N.HCl$ separates as precipitate. After a stirring period of 5 hours the 4,5,5-trifluoro-4-trifluoromethyl-1,3-dioxolane distills off. Its boiling point is the same as that of the product of Example 4. Yield 55% of the theory.

EXAMPLE 6

A 2 liter flask provided with KPG stirrer, thermometer, dropping funnel and distillation column is charged with a solution of 436 g (3.6 mols) of $(C_2H_5)_3N.HF$ in 1,100 ml of dry n-butyronitrile. While stirring and occasionally cooling in an ice bath 368 g (1.51 mols) of $CF_3CF(OCHCL-CH_3)COCl$ are added dropwise at a temperature of from 14° to 42° C. $(C_2H_5)_3N.HCl$ separates as precipitate. The reaction mixture is stirred for 4 hours at 34° to 38° C. and then left to stand overnight at room temperature whereupon the 4,5,5-trifluoro-2-methyl-4-trifluoromethyl-1,3-dioxolane still containing a small proportion of $(C_2H_5)_3N$ is distilled off. The distillate is washed with water, dilute $H_2SO_4$ and $NaHCO_3$ solution and dried over $MgSO_4$. The fractional distillation yields 270 g (1.28 mols) of a product boiling at 71° to 72° C. under 758 torr (85% of theory).

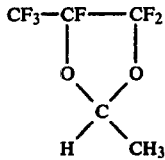

Molecular weight: 210.
Calc.: C 28.57%; H 1.90%; F 54.28%; Found: C 28.8%; H 1.90%; F 53.7%.

Under identical conditions can be obtained:

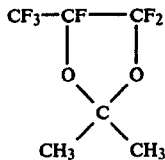

Molecular weight: 224.
Calc.: C 32.14%; H 2.68%; F 50.89%; Found: C 32.20%; H 2.7%; F 50.6%.

Boiling point 85.4° C. under 761 torr, yield 64%.

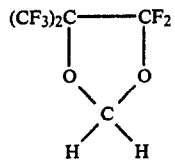

Molecular weight: 246.
Calc.: C 24.39%; H 0.81%; F 61.79%.

EXAMPLE 7

200 g (1.13 mols) of $CH_3CHCl-O-CF_2COF$ are added dropwise over a period of 75 minutes to 206 g (1.7 mols) of $(C_2H_5)_3N.HF$ kept in the liquid state by heating to 55° C. While cooling with air the temperature of the reaction mixture rises to 71° C. 2-Methyl-4,4,5,5-tetrafluoro-1,3-dioxolane passes at 56° C. into the receiver via the distillation column mounted on the reaction flask. Further heating of the mixture to 162° C. over a period of 4 hours yields a total amount of 166 g of crude distillate. A redistillation over a 30 cm column packed with Raschig rings gives 143 g of pure product boiling at 54° to 55° C. under 745 torr, corresponding to 79% of the theory.

What is claimed is:

1. A process for the manufacture of 4,5-perfluoro-1,3-dioxolanes of the formula

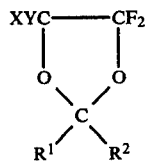

in which X and Y, independent of one another, are fluorine or trifluoromethyl and $R^1$ and $R^2$ are hydrogen or methyl, which comprises reacting a 2-(α-chloroalkoxy)-perfluorocarboxylic acid halide of the formula $$R^1R^2CCl-O-CXY-COZ$$

in which X, Y, $R^1$ and $R^2$ are as defined above and Z is chlorine or fluorine, with a fluoride selected from the group consisting of potassium fluoride, cesium fluoride, ammonium fluoride and alkylammonium fluoride, under anhydrous conditions, the reaction being conducted at a temperature in the range of from 0° to 120° C.

2. The process of claim 1, wherein the fluoride reacted is present in an excess of 10 to 50 mol %, calculated on the gram-atoms of chlorine present per mol of 2-(α-chloroalkoxy)-perfluorocarboxylic acid halide.

3. The process of claim 1, wherein said reaction is carried out in the presence of an aprotic polar solvent.

4. The process of claim 3, wherein said aprotic polar solvent is selected from the group consisting of nitrile, acid amide, polyether, dimethyl sulfoxide and sulfolane.

5. The process of claim 3, wherein said aprotic polar solvent is selected from the group consisting of nitrile, dimethyl formamide, dioxane and diethylene glycol dimethyl ether.

* * * * *